United States Patent
Gedenk et al.

(10) Patent No.: US 7,484,719 B2
(45) Date of Patent: Feb. 3, 2009

(54) SPRING ELEMENT FOR RAIL VEHICLES

(75) Inventors: Volker Gedenk, Hemmingen (DE);
Andreas Kropf, Burgdorf (DE);
Friedrich Hoppmann, Hemmingen (DE)

(73) Assignee: ContiTech Luftfedersysteme GmbH, Hannover (DE)

( * ) Notice: Subject to any disclaimer, the term of this patent is extended or adjusted under 35 U.S.C. 154(b) by 0 days.

(21) Appl. No.: 10/587,847

(22) PCT Filed: Dec. 8, 2004

(86) PCT No.: PCT/EP2004/053326

§ 371 (c)(1),
(2), (4) Date: Sep. 28, 2006

(87) PCT Pub. No.: WO2005/073588

PCT Pub. Date: Aug. 11, 2005

(65) Prior Publication Data

US 2007/0158886 A1    Jul. 12, 2007

(30) Foreign Application Priority Data

Jan. 29, 2004    (EP)    ................................. 04001874.9

(51) Int. Cl.
*F16F 9/04*    (2006.01)
(52) U.S. Cl. ................................. 267/64.24; 267/64.21
(58) Field of Classification Search ... 267/64.21–64.27, 267/122
See application file for complete search history.

(56) References Cited

U.S. PATENT DOCUMENTS 2,966,366 A * 12/1960 Moulton ...................... 280/104

(Continued)

FOREIGN PATENT DOCUMENTS

GB    1078641    8/1967
KR    20-0032657    7/1986

*Primary Examiner*—Christopher P Schwartz
(74) *Attorney, Agent, or Firm*—Walter Ottesen

(57) ABSTRACT

A spring element (2) consists essentially of an elastic spring body (4) which is fixed between two rigid end parts (6, 8) arranged at a variable spacing from each other. The spring body (4) consisting of rubber or a rubber-type plastic has a rotationally symmetrical cross section, the longitudinal section shows a biconvex surface line. A U-shaped cross section is formed as a result of a cavity (10). The abrasion caused by the introduction of vertical and horizontal forces is to be reduced and an easy, horizontal slide is to be made possible. The surface (12) of the spring body (4) is provided with ribs (14; 14a, . . . ) that are arranged at spacings (A) from each other and are intersected by ribs (16; 16a, . . . ) or groups of ribs (16, . . . ) also arranged at spacings (A) from each other. Polygonal fields (18a, . . . ) are formed on the surface (12) of the spring body (4) in the gaps between the ribs (14, . . . ; 16, . . . ) according to the angle of intersection. Instead of the ribbing, or in addition thereto, the spring body (4) and/or the surface of at least one of the end bodies (6 and/or 8) can be provided with a smooth surface. The ribs (14a, . . . ; 16a, . . . ) are preferably approximately 2 mm thick and approximately 10 mm apart. The spring element is especially used as an additional spring combined with a pneumatic spring in rail vehicles.

19 Claims, 2 Drawing Sheets

U.S. PATENT DOCUMENTS

| | | |
|---|---|---|
| 3,300,257 A | 1/1967 | Selker et al. |
| 3,598,155 A * | 8/1971 | Burkley .................. 267/64.27 |
| 4,092,017 A * | 5/1978 | Urushiyama et al. ..... 267/64.23 |
| 4,386,791 A * | 6/1983 | Watanabe ................ 280/6.157 |
| 4,564,177 A | 1/1986 | Leonard |
| 4,690,388 A | 9/1987 | Harrison |
| 4,715,588 A * | 12/1987 | Drescher et al. ............ 267/122 |
| 4,718,649 A * | 1/1988 | Pohlmann et al. ........ 267/64.24 |
| 4,781,365 A | 11/1988 | Harrison |
| 4,921,223 A * | 5/1990 | Fukumura et al. ........ 267/64.23 |

* cited by examiner

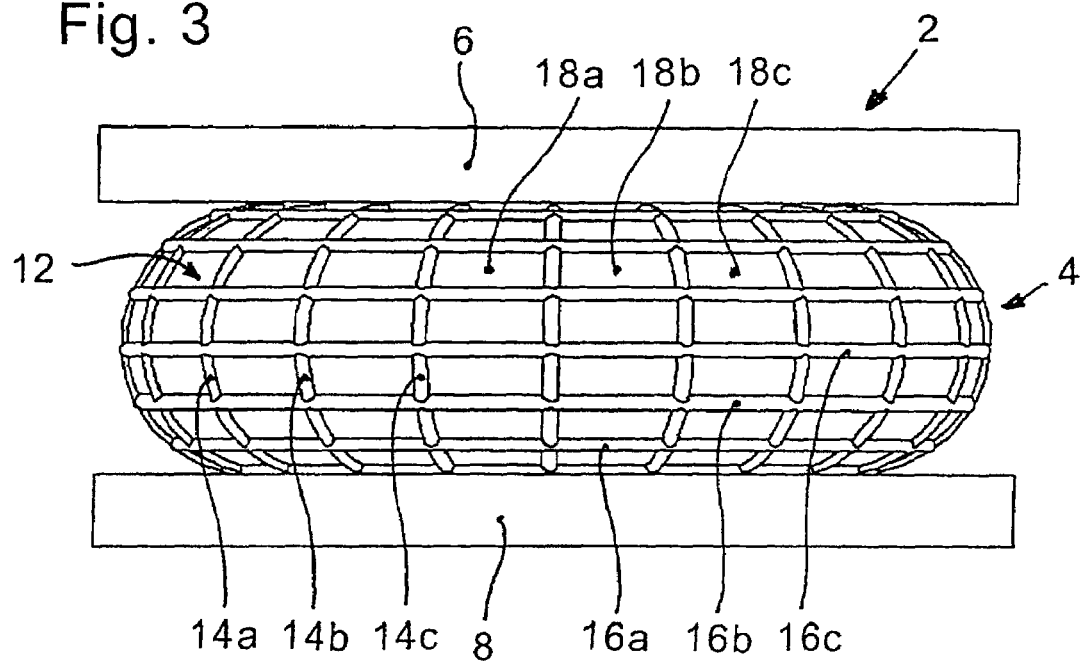
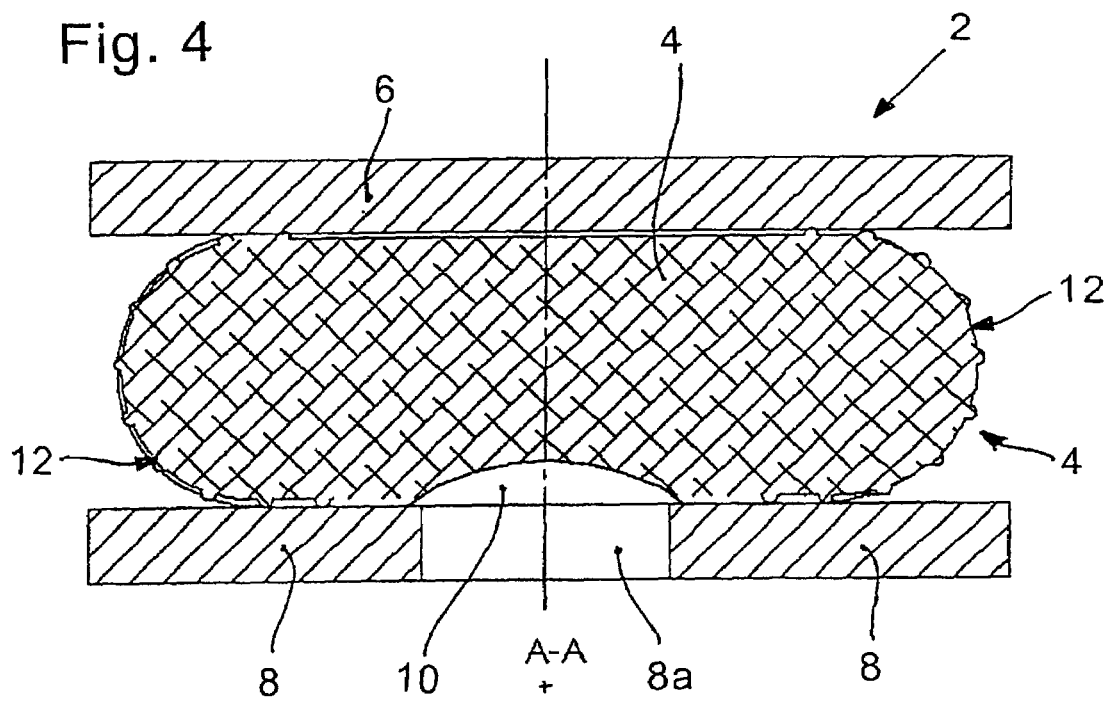

SPRING ELEMENT FOR RAIL VEHICLES

RELATED APPLICATION

This application is the national stage of PCT/EP 2004/053326, filed Dec. 8, 2004, designating the United States and claiming priority from European patent application no. 04001874.9, filed Jan. 29, 2004, the entire contents of which are incorporated herein by reference.

FIELD OF THE INVENTION

The invention relates to a spring element and especially to a so-called layer spring which can be used by itself or as an ancillary spring in combination with an air spring in a railroad vehicle.

BACKGROUND OF THE INVENTION

A spring element for vehicle suspensions is disclosed in the U.S. Pat. Nos. 4,781,365 and 4,690,388. The essential features of this spring element are described in the first paragraphs of the respective disclosures.

The outer contour of the rubber body of the known spring element is smooth. Because of continuously alternating vertical forces, the support surface of the rubber body increases and decreases. The rubber body rolls off on the lower support because of the additionally introduced horizontal forces. Both result in relative movements between the rubber and the support and therefore in friction and wear of the rubber.

SUMMARY OF THE INVENTION

The spring element known from the above-mentioned state of the art is to be improved in such a manner that, during the introduction of vertical and horizontal forces, the wear of the rubber is reduced and an easy horizontal sliding is made possible.

The spring element of the invention affords the advantage with respect to the known springs that the ribs on the spring surface form small polygons, especially quadrilaterals (rhombi, rectangles, squares). When the spring element is pressed onto the support, air collects in these polygons. For this reason, the spring body slides on a plurality of air pillows. Therefore, there is only friction between the rubber ribs and the support surface.

In lieu of the ribbed spring surface or additionally, the entire surface of the spring body including possibly the rib surface and/or the surface of the rigid end bodies arranged relative to each other at a variable spacing can be provided with a sliding surface whereby an abrading action is substantially avoided during the deformation of the loaded spring body.

In a constructive configuration of the ribs arranged on the spring body, it has been shown to be especially advantageous when the ribs are approximately 2 mm high and are mutually spaced approximately 10 mm from each other.

The surface of the ribs can be made from a slide capable material in order to further reduce the coefficient of friction of the spring body. The ribs are preferably configured as so-called wear ribs with the material of these wear ribs being different from the material of the spring body.

The ribs are so configured and dimensioned that they outlive the time of use of the spring element.

With the different measures, a longer use time of the spring element is ensured. The characteristic line of the spring is not influenced by the different friction on the support surface.

BRIEF DESCRIPTION OF THE DRAWINGS

The invention will now be described with reference to the drawings wherein:

FIG. 3 is a front elevation view of the same spring element shown in the loaded state; and, FIG. 4 is a vertical longitudinal section view of the same spring element likewise in the loaded state.

DESCRIPTION OF THE PREFERRED EMBODIMENTS OF THE INVENTION

The spring element 2 shown in FIGS. 1 to 4 is a so-called layer spring which can be used by itself as a support spring but also as an additional spring in combination with an air spring for supporting the chassis of a rail vehicle.

The spring element 2 essentially comprises an elastic spring body 4 which is attached between two rigid members (6, 8) which are arranged at a variable spacing from each other.

The spring body 4 has a rotationally symmetrical cross section. The longitudinal section (FIGS. 2 and 4) shows an approximately biconvex surface line. A U-shaped cross section results overall because of a cavity 10.

Figure 2:
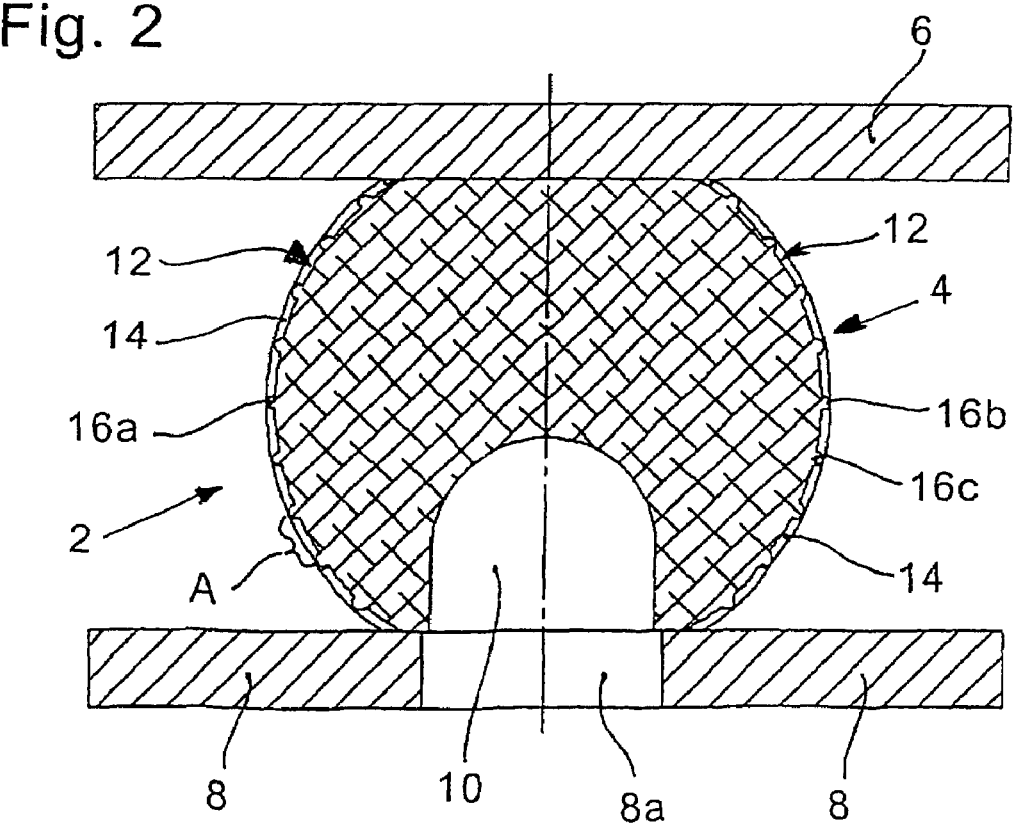
FIG. 2 is a vertical longitudinal section view of the same spring element likewise in the unloaded state.

The spring body 4 is a monolithic body as shown in the section views of FIGS. 2 and 4 and is made of rubber or an elastomeric material of comparable elastic characteristics.

The rigid upper end member 6 has a disc shape and the rigid lower end member 8 is of annular configuration. More specifically, the lower end member 8 has an opening 8a at its center whereby the cavity 10, which is provided in the spring body 4, is connected to the ambient.

The above described assembly is known from the state of the art and is not the object of the present invention. The present invention is directed to the surface configuration of such spring bodies 4.

Figure 1:
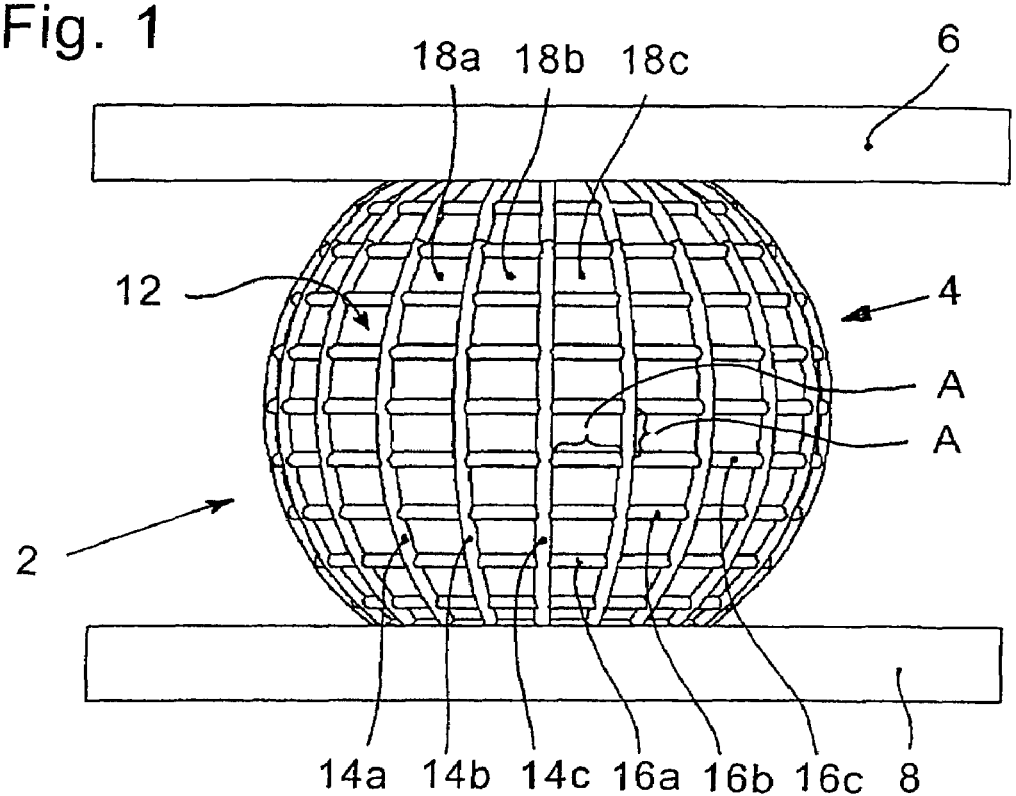
FIG. 1 is a front elevation view of a spring element of the invention shown in the unloaded state.

As can especially be seen in the lateral views of FIGS. 1 and 3, perpendicularly running ribs 14a and horizontally running ribs 16a are arranged on the surface 12 of the spring body 4 in the manner of degrees of longitude and latitude on a globe. These ribs (14a, . . . ) and (16a, . . . ) are approximately 2 mm thick and are positioned at spacings A of approximately 10 mm from each other on the surface 12 whereby a plurality of small enclosed quadrilaterals (18a, . . . ) is formed.

When the spring body 4 is pressed against the end members (6, 8) functioning as supports, the air builds up which is trapped within the quadrilaterals (18a, . . . ) between the spring body 4 and the support 6 and/or support 8. When the relative dimensions between the spring body 4 and the respective supports 6 and 8 change with respect to each other because of forces acting on the spring 2, then the spring body 4 does not rub on the supports 6 and 8, but instead, the spring body 4 consisting of rubber slides on the many small air pillows. The above force action can be vertical as well as horizontal whereby a movement in the corresponding direction results. In this way, there is friction only between the rubber ribs (14a, . . . ) and (16a, . . . ) and the respective surfaces of the supports 6 and 8.

| REFERENCE NUMERALS | |
| --- | --- |
| 2 | spring element |
| 4 | spring body |
| 6, 8 | end members, support(s) |
| 6 | upper disc-shaped support member |
| 8 | lower annularly-shaped support member |
| 8a | opening in the lower support member |
| 10 | cavity |
| 12 | surface of the spring body |
| 14; 14a, . . . | perpendicular ribs on the spring body |
| 16; 16a, . . . | horizontal ribs on the spring body |
| A | spacing between two ribs |
| 18a, . . . | quadrilaterals, fields enclosed by ribs (14, 16) |

The invention claimed is:

1. A spring comprising:

first and second rigid end members moveable relative to each other causing the distance therebetween to vary during operation of said spring;

an elastic spring body mounted between said end members;

said elastic spring body having a rotationally symmetrical cross section and a longitudinal section having biconvex shape;

said elastic spring body being a monolithic body of rubber or a rubber-like plastic and having a surface which is pressed with more or less area of said surface against said rigid end members as said distance becomes shorter or longer during said operation;

a first plurality of ribs arranged on said surface spaced one from the other at respective first distances;

a second plurality of ribs arranged on said surface spaced one from the other at respective second distances;

said second plurality of ribs intersecting said first plurality of ribs so as to form a multiplicity of intermediate spaces defining a corresponding plurality of polygonal areas or cavities on said surface wherein air collects to become trapped between said spring body and said rigid end members to form a plurality of air pillows as said rigid end members move toward each other so as to permit said elastic spring body to slide on said air pillows;

said elastic spring body having a substantially U-shaped cavity formed therein so as to impart said biconvex shape to said elastic spring body when viewed in longitudinal section; and, one of said rigid end members having an opening formed therein lying opposite said U-shaped cavity to permit said U-shaped cavity to communicate with the ambient.

2. The spring of claim 1, wherein a surface coating to facilitate sliding is provided on at least one of said elastic spring body, said first end member and said second end member.

3. The spring of claim 2, wherein said first plurality of ribs are mutually parallel and said second plurality of ribs are mutually parallel and intersect said first plurality of ribs orthogonally.

4. The spring of claim 3, wherein said first plurality of ribs are spaced approximately 10 mm one from the other; and, said second plurality of ribs are spaced approximately 10 mm one from the other.

5. The spring of claim 4, wherein said ribs each have a height of approximately 2 mm.

6. The spring of claim 5, wherein said ribs are configured as wear or abrasion ribs.

7. The spring of claim 6, wherein said ribs are made of a material which differs from the material of said spring body.

8. The spring of claim 7, wherein said ribs have a surface to facilitate sliding.

9. The spring of claim 1, wherein the ribs of said first and second plurality of ribs all have the same height.

10. The spring of claim 1, wherein said one rigid end member is a flat annular member defining said opening; and, the other one of said rigid end members is a flat disc-shaped member.

11. A spring comprising:

first and second rigid end members moveable relative to each other causing the distance therebetween to vary;

an elastic spring body mounted between said end members so as to act solely by itself as a spring between said rigid end members;

said elastic spring body having a rotationally symmetrical cross section and a longitudinal section having biconvex shape;

said elastic spring body having a surface and being a monolithic body of rubber or a rubber-like plastic;

a first plurality of ribs arranged on said surface spaced one from the other at respective first distances and said first plurality of ribs having a predetermined height;

a second plurality of ribs arranged on said surface spaced one from the other at respective second distances and said second plurality of ribs having a height equal to said predetermined height;

said second plurality of ribs intersecting said first plurality of ribs so as to form a multiplicity of intermediate spaces defining a corresponding plurality of polygonal cavities on said surface wherein air collects to become trapped between said spring body and said rigid end members to form a plurality of air pillows as said rigid end members move toward each other so as to permit said elastic spring body to slide on said air pillows;

said elastic spring body having a cavity formed therein so as to impart said biconvex shape to said elastic spring body when viewed in longitudinal section; and, one of said rigid end members having an opening formed therein lying opposite said cavity to permit said cavity to communicate with the ambient.

12. The spring of claim 11, wherein a surface coating to facilitate sliding is provided on at least one of said elastic spring body, said first end member and said second end member.

13. The spring of claim 12, wherein said first plurality of ribs are mutually parallel and said second plurality of ribs are mutually parallel and intersect said first plurality of ribs orthogonally.

14. The spring of claim 13, wherein said first plurality of ribs are spaced approximately 10 mm one from the other; and, said second plurality of ribs are spaced approximately 10 mm one from the other.

15. The spring of claim 14, wherein said ribs each have a height of approximately 2 mm.

16. The spring of claim 15, wherein said ribs are configured as wear or abrasion ribs.

17. The spring of claim 16, wherein said ribs are made of a material which differs from the material of said spring body.

18. The spring of claim 17, wherein said ribs have a surface to facilitate sliding.

19. The spring of claim 11, wherein said one rigid end member is a flat annular member defining said opening; and, the other one of said rigid end members is a flat disc-shaped member.

\* \* \* \* \*